US012758746B2

(12) United States Patent
Thomas et al.

(10) Patent No.: US 12,758,746 B2
(45) Date of Patent: *Oct. 13, 2026

(54) SYSTEMS AND DEVICES FOR ATRAUMATIC CATHETER INSERTION ALONG A GUIDEWIRE

(71) Applicant: MicroLiner Technologies, Inc., Mt. Pleasant, SC (US)

(72) Inventors: Alexander R. Thomas, Charlotte, NC (US); Todd O. Flohr, Mt. Pleasant, SC (US); William Preston Buchanan, Wilmington, NC (US)

(73) Assignee: MicroLiner Technologies, Inc., Mt. Pleasant, SC (US)

( * ) Notice: Subject to any disclaimer, the term of this patent is extended or adjusted under 35 U.S.C. 154(b) by 1022 days.

This patent is subject to a terminal disclaimer.

(21) Appl. No.: 17/935,247

(22) Filed: Sep. 26, 2022

(65) Prior Publication Data

US 2023/0013948 A1 Jan. 19, 2023

Related U.S. Application Data

(63) Continuation of application No. 17/558,020, filed on Dec. 21, 2021, now Pat. No. 11,452,849.

(Continued)

(51) Int. Cl.

| | |
|---|---|
| ***A61M 25/06*** | (2006.01) |
| ***A61M 25/00*** | (2006.01) |
| *A61M 25/01* | (2006.01) |

(52) U.S. Cl.

CPC .... *A61M 25/0662* (2013.01); *A61M 25/0053* (2013.01); *A61M 25/0108* (2013.01);

(Continued)

(58) Field of Classification Search

CPC .......... A61M 25/0053; A61M 25/0067; A61M 25/0108; A61M 25/0169; A61M 25/065;

(Continued)

(56) References Cited

U.S. PATENT DOCUMENTS

| | | | |
|---|---|---|---|
| 5,120,323 | A | 6/1992 | Shockey et al. |
| 5,292,332 | A | 3/1994 | Lee |

(Continued)

FOREIGN PATENT DOCUMENTS

| | | | |
|---|---|---|---|
| JP | 2008142351 | A | 6/2008 |
| JP | 2010528776 | A | 8/2010 |

(Continued)

OTHER PUBLICATIONS

WIPO, International Preliminary Report on Patentability for corresponding PCT Patent Application No. PCT/US22/12270, dated Jul. 20, 2023, 7 pages.

(Continued)

*Primary Examiner* — Kami A Bosworth
(74) *Attorney, Agent, or Firm* — NK Patent Law

(57) ABSTRACT

A catheter system for atraumatic placement along a guidewire includes: a catheter including a cylindrical catheter body that defines a longitudinally extending interior lumen; and a guide device. The guide device includes: a conduit member for insertion into the interior lumen of the catheter body; a leading structure connected to a forward end of the conduit member, the leading structure including a cone and a sleeve extending forward from the cone; and an inner guide hole extending longitudinally through the leading structure and conduit member. In use, the guide device and catheter body are coaxially arranged, the cone is forward of the catheter, and the sleeve extends forward from the cone. The cone includes a shoulder, and a tapered exterior that increases diametrically from the sleeve to the shoulder.

(Continued)

The shoulder abuts a distal end of the catheter to register insertion of the guide device in the catheter.

14 Claims, 9 Drawing Sheets

Related U.S. Application Data

(60) Provisional application No. 63/140,610, filed on Jan. 22, 2021.

(52) U.S. Cl.
CPC ............... *A61M 2025/0681* (2013.01); *A61M 2025/0687* (2013.01)

(58) Field of Classification Search
CPC ...... A61M 25/0662; A61M 2025/0681; A61M 2025/0687; A61M 25/007; A61M 2025/006; A61M 2025/0062; A61M 2025/0079
See application file for complete search history.

(56) References Cited

U.S. PATENT DOCUMENTS

| | | | | |
|---|---|---|---|---|
| 5,762,631 | A * | 6/1998 | Klein | A61M 25/0023 264/171.12 |
| 6,120,480 | A * | 9/2000 | Zhang | A61M 25/0662 604/164.01 |
| 8,048,032 | B2 | 11/2011 | Root et al. | |
| 8,142,413 | B2 | 3/2012 | Root et al. | |
| 8,292,850 | B2 | 10/2012 | Root et al. | |
| 8,690,936 | B2 | 4/2014 | Nguyen et al. | |
| 9,301,840 | B2 | 4/2016 | Nguyen et al. | |
| RE46,116 | E | 8/2016 | Root et al. | |
| 10,124,146 | B2 | 11/2018 | Di Caprio et al. | |
| 10,456,555 | B2 | 10/2019 | Garrison et al. | |
| 2001/0027295 | A1 | 10/2001 | Dulak et al. | |
| 2003/0065353 | A1 | 4/2003 | Horzewski et al. | |
| 2006/0178739 | A1 | 8/2006 | Shalaby et al. | |
| 2006/0263145 | A1 | 11/2006 | Pal | |
| 2011/0270229 | A1 | 11/2011 | Tanaka et al. | |
| 2014/0012281 | A1 | 1/2014 | Wang et al. | |
| 2014/0018773 | A1 | 1/2014 | Wang et al. | |
| 2015/0265802 | A1 | 9/2015 | Fukuoka et al. | |
| 2015/0265803 | A1 | 9/2015 | Ahme et al. | |
| 2015/0273182 | A1 | 10/2015 | Watanabe et al. | |
| 2017/0021130 | A1 | 1/2017 | Dye | |
| 2017/0252043 | A1 | 9/2017 | Fuller et al. | |
| 2018/0200478 | A1 | 7/2018 | Lorenzo et al. | |
| 2020/0086095 | A1 * | 3/2020 | Kleinhaus | A61B 17/3478 |

FOREIGN PATENT DOCUMENTS

| | | | |
|---|---|---|---|
| JP | 2019514523 | A | 6/2019 |
| JP | 2020513938 | A | 5/2020 |
| WO | 2010073646 | A1 | 7/2010 |
| WO | 2011086758 | A1 | 7/2011 |
| WO | 2018092387 | A1 | 5/2018 |

OTHER PUBLICATIONS

EPO, Extended European Search Report for corresponding European Patent Application No. 22742999.0, mailed Nov. 5, 2024, 9 pages.
ISA/US, International Search Report and Written Opinion in corresponding PCT Patent Application No. PCT/US2022/012270, mailed Apr. 4, 2022, 8 pages.
USPTO, Non-Final Office Action for corresponding U.S. Appl. No. 17/558,020, dated Feb. 24, 2022, 12 pages.
JPO, Office Action for corresponding Japanese Patent Application No. 2023-544267, Jul. 22, 2025, 8 pages including translation.

* cited by examiner

SYSTEMS AND DEVICES FOR ATRAUMATIC CATHETER INSERTION ALONG A GUIDEWIRE

CROSS-REFERENCE TO RELATED APPLICATION

This application is a continuation application of U.S. patent application Ser. No. 17/558,020, titled "SYSTEMS AND DEVICES FOR ATRAUMATIC CATHETER INSERTION ALONG A GUIDEWIRE," filed on Dec. 21, 2021 and being issued as U.S. Pat. No. 11,452,849 on Sep. 27, 2022, which claims the benefit of priority of U.S. provisional patent application No. 63/140,610, titled "MEDICAL DEVICE, METHOD OF MAKING AND USING SAME," filed on Jan. 22, 2021, which are all incorporated herein in their entireties by this reference.

TECHNICAL FIELD

This disclosure relates generally to medical devices and methods. More particularly, this disclosure relates to devices and systems for atraumatic placement and use of a catheter.

BACKGROUND

A catheter as used in surgical procedures is a thin tube inserted in a patient to perform a surgical procedure and/or place a prosthetic device, such as a coronary artery stent. Catheters can be particularly designed for cardiovascular, urological, gastrointestinal, neurovascular, and ophthalmic applications. The process of inserting a catheter is called "catheterization."

A guidewire is typically used to guide the catheter into place. Insertion and placement of the guidewire typically precedes placement of the catheter. A guidewire gains access to the blood vessels and other body conduits, and, once placed, guides entry and advance of a catheter, which follows the path of guidewire.

The advancing end of a catheter, as it follows the guidewire, encounters tissue that must yield and/or stretch to accommodate the outer diameter of the catheter, which is greater than that of the guidewire. Even when the exterior diameter of a guidewire is as well matched as feasible with the interior diameter of a catheter, which is preferably allowed to slide fairly freely along the guidewire, the advancing end of the catheter typically approaches effectively as a potentially dramatic diameter step increase, instead of a smoothly increasing diameter function. The blunt end of an advancing catheter can thus traumatize tissue along the way.

Furthermore, in some instances, fluid along the catheter, even during catheterization as the catheter moves along a guidewire, is preferred. However, the closer the exterior diameter of a guidewire matches the interior diameter of the catheter, the more assuredly any fluid flow, such as blood flow, is blocked within the catheter by the guidewire. Thus, even close matching the guidewire and catheter using current such devices has its drawbacks.

SUMMARY

This summary is provided to briefly introduce concepts that are further described in the following detailed descriptions. This summary is not intended to identify key features or essential features of the claimed subject matter, nor is it to be construed as limiting the scope of the claimed subject matter.

A catheter system for atraumatic placement along a guidewire, according to at least one embodiment, includes: a catheter including a cylindrical catheter body that defines a longitudinally extending interior lumen; and a guide device. The guide device includes: a conduit member for insertion into the interior lumen of the catheter body; a leading structure connected to a forward end of the conduit member, the leading structure including a cone and a sleeve extending forward from the cone; and an inner guide hole extending longitudinally through the leading structure and conduit member. In use, the guide device and catheter body are coaxially arranged, the cone is forward of the catheter, and the sleeve extends forward from the cone.

The cone may include a shoulder, and a tapered exterior that increases diametrically from the sleeve to the shoulder. A back of the shoulder can abut a distal end of the catheter to register insertion of the guide device in the catheter.

In at least one example, an outer diameter of the shoulder uncompressed is greater than an inner diameter of the lumen of the catheter body; and the cone is deformable to permit deformation to pass the shoulder through the distal end and into and along the lumen.

The conduit member may include a fluted exterior having grooves.

The cone may include slots that are connected to the grooves for fluid passage.

The grooves may extend longitudinally along the exterior of the conduit member.

The grooves can be evenly distributed around the exterior of the conduit member.

The guide device may include a proximal member, for physical control of the guide device, attached to a rearward end of the conduit member offset from the guide hole.

The inner guide hole may have a uniform inner diameter along the sleeve, cone, and conduit member.

The catheter body, in at least one example, has a rearward end and an opposite distal end, the rearward end of the catheter body has a tapered entrance, and the interior lumen extends from the tapered entrance to the distal end.

The catheter body may have a longitudinally extending layered wall including a stiffening member, and inner liner, and an outer cover.

The stiffening member may include a helical spring extending from the tapered entrance toward the distal end.

The inner liner may extend within the stiffening member and define an interior surface of the interior lumen. The outer cover may surround the stiffening member and define an exterior surface of the catheter body.

The catheter can include a radiopaque marker or radiopaque material doping at the proximate or the distal end.

The radiopaque marker may include a cylindrical band forward of the stiffening member, between the outer cover and inner liner, and rearward of the distal end or radiopaque material integrated into the material.

The above summary is to be understood as cumulative and inclusive. The above described embodiments and features are combined in various combinations in whole or in part in one or more other embodiments.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
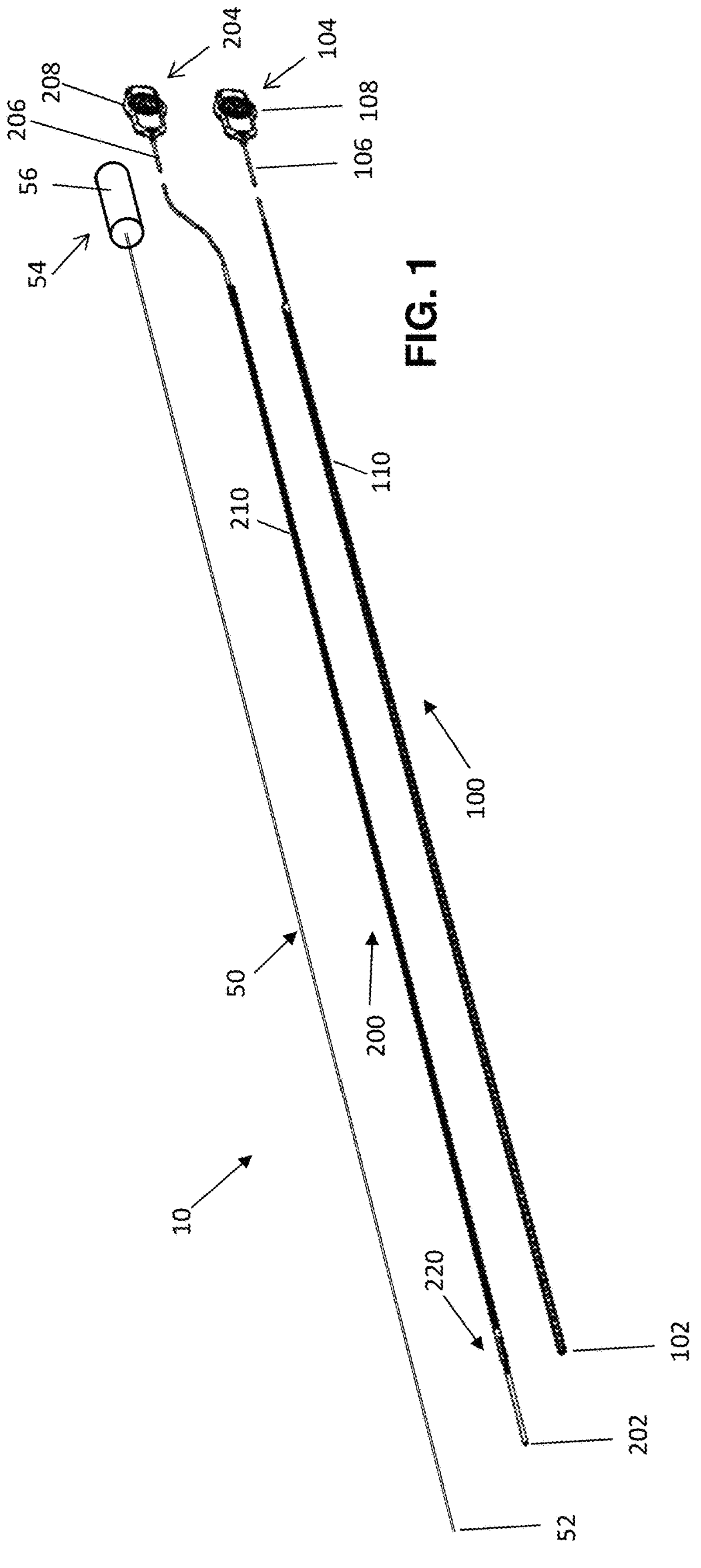
FIG. 1 is a perspective view of a system, according to at least one embodiment, including a guidewire, a novel catheter, and a novel guide device for atraumatic insertion of the catheter along the guidewire.
Figure 2:
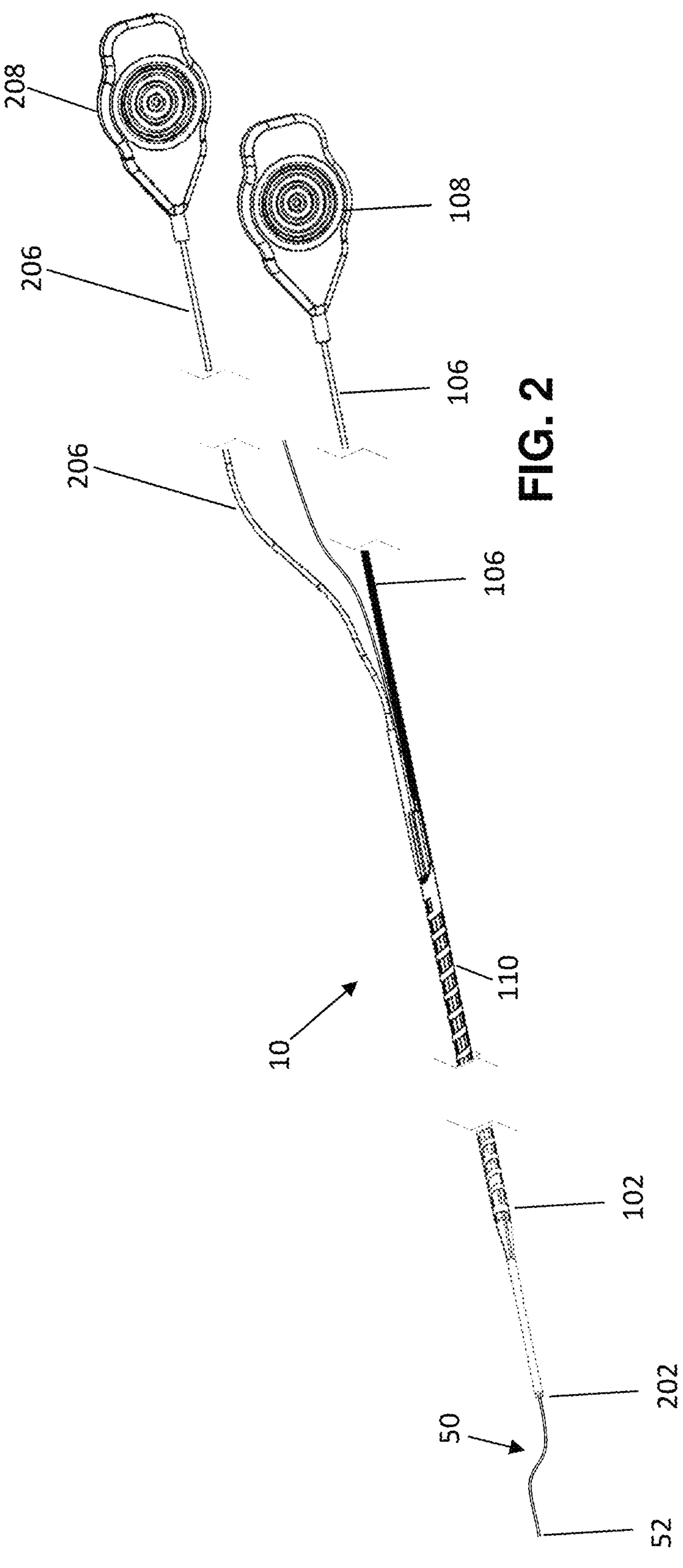
FIG. 2 is an enlarged perspective view of the guidewire, catheter, and guide device of FIG. 1 shown assembled and with lengths thereof redacted for convenience in illustration.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although steps may be expressly described or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Like reference numbers used throughout the drawings depict like or similar elements. Unless described or implied as exclusive alternatives, features throughout the drawings and descriptions should be taken as cumulative, such that features expressly associated with some particular embodiments can be combined with other embodiments.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Unless indicated to the contrary, the numerical parameters set forth in the instant specification and attached claims are approximations that can vary depending upon the desired properties sought to be obtained within the scope of these descriptions. As used herein, the term "approximately", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are within the scope of these descriptions.

According to the below described particular embodiments, with reference to the drawings, and those further embodiments and examples implied or understood within the full scope of these descriptions and drawings, an improved system for atraumatic insertion of a catheter into a surgical site along a guidewire is provided. A guide device is assembled with a catheter to guide the distal end of the catheter into the surgical site. The guide device and catheter are coaxially arranged around the guide wire, with the guide device extending like a sleeve between the guide wire and catheter. The forward end of the assembled guide device and catheter has effectively a tapered forward transition to the outer diameter of the catheter for atraumatic advance along the guide wire. The guide device permits blood flow within the catheter. Once the catheter is positioned, the guidewire and guide device can be removed from the catheter. The catheter can then be used conventionally, for example for the placement of implant devices such as stents.

FIG. 1 illustrates a novel catheter 100, and a novel guide device 200, which can be referenced together as a catheter system 10, with or without the guidewire 50. The guidewire 50 may be of a commercially available type present in the prior art. However, when provided in combination with the catheter 100 and guide device 200, such combination, including even a prior-art guidewire, is novel and advantageous as described below due to features of the catheter 100 and/or guide device 200.

A guidewire 50 is typically a metal wire or spring used as a guide for placement of a larger device or prosthesis, such as a catheter. A guidewire is used to enter tight spaces, e.g., obstructed valves or channels, within the body, or to assist in inserting, positioning, and moving a catheter. Guidewires vary in size, length, stiffness, composition, and shape of the distal tip 52. Some guidewires have a hooked distal tip, and some are steerable from the proximal end 54 so as to navigate tortuous paths within patient anatomy. The guidewire 50 is illustrated as having a device 56 at the proximal end 54, which may represent a basic handle, clamp, or chuck, and may represent a manipulation device by which the guidewire 50 can be steered, for example by actuation of the distal tip 52, or otherwise gripped or controlled. The guidewire 50 thus generically represents many guidewire types for use with the inventive system 10.

The terms “proximal” and “distal” as used herein refer to a user's perspective, such as a surgeon. For example, a proximal portion of a device or structure can be grasped and manipulated as a distal portion enters an incision and is advanced within a patient's anatomy to a site where a procedure is to be conducted or a prosthetic device is to be placed, deployed, or maneuvered. Similarly, the terms “forward” and “front” as used herein refer to the direction of advancement into a surgical site, whereas “rearward” and “back” refer to the opposite direction of withdrawal. Of course, the devices and structures described herein may be placed together or apart in arbitrary orientations when carried and stored. Nonetheless, relative terms such as these are useful for description and distinction of structures and features without ambiguity. The term “longitudinal” refers to dimensions and directions along the described structures from proximal to distal, whereas “radial” and “diametric” refer to dimensions and directions perpendicular thereto.

Figure 3:
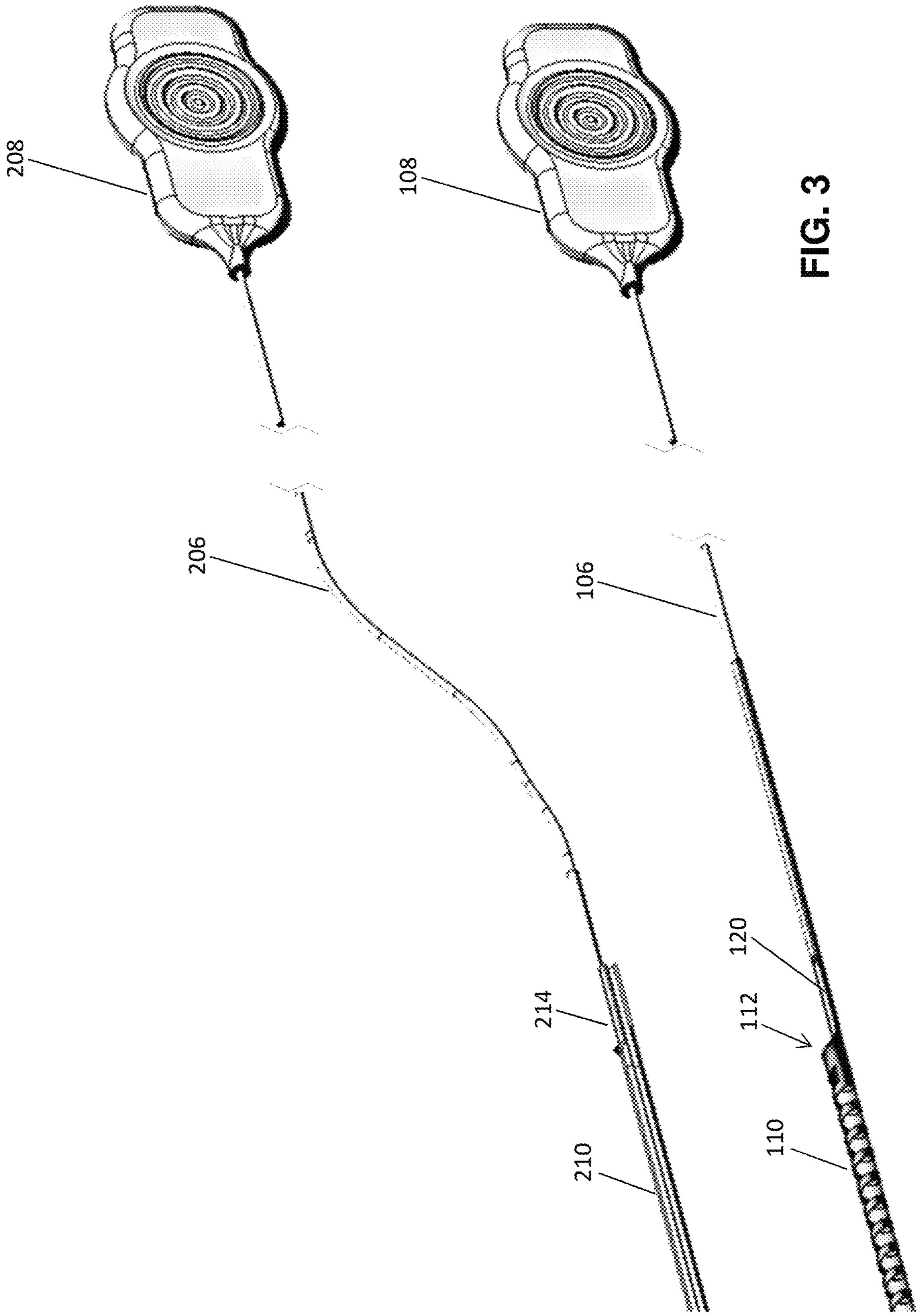
FIG. 3 is a further enlarged perspective view of proximal and medial portions of each of the catheter and guide device of FIG. 1, shown with lengths therebetween redacted for convenience in illustration.
Figure 10:
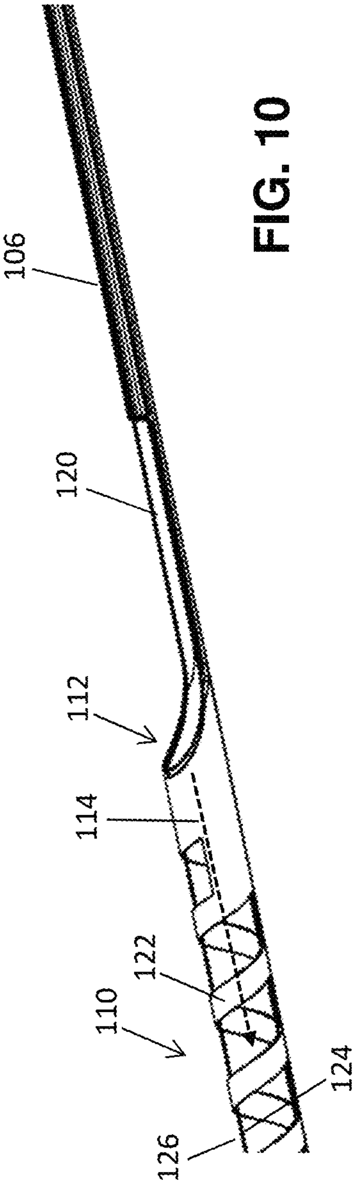
FIG. 10 is an enlarged perspective view, in correspondence with FIG. 9, of the rearward entrance area of the lumen of the catheter of FIG. 1.

As shown in FIG. 1, the catheter 100 can accordingly be described as having a distal end 102 and a proximal end 104. A proximal member 106, for physical control and handling of the catheter, extends forward from the proximal end 104 toward a tapered rearward entrance 112 of a hollow cylindrical catheter body 110 that defines an interior lumen 114 (FIG. 4A) as also shown in FIG. 3 and FIG. 10. The tubular catheter body 110 extends forward from the rearward entrance 112 to the distal end 102. In the illustrated embodiment, the catheter 100 includes a handle 108 attached to the proximal member 106 at the proximal end 104 for comfortable and assured grip and control of the catheter 100. The proximal member 106 is illustrated as a wire that is flexible, semi-rigid, resilient, and durable. Components forward of the handle 108 can be likewise be similarly described as flexible, semi-rigid, resilient, and durable to support their insertion into a surgical site in use.

Figure 4A:
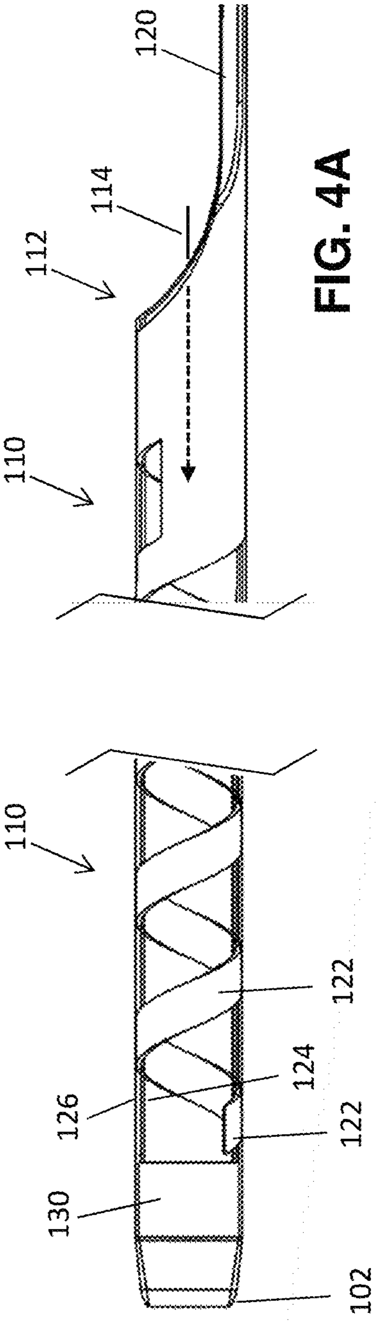
FIG. 4A is an enlarged view of the distal end of the catheter of FIG. 1, and the rearward entrance area of the lumen of the catheter, shown with a length of the catheter body therebetween redacted for convenience in illustration.
Figure 4B:
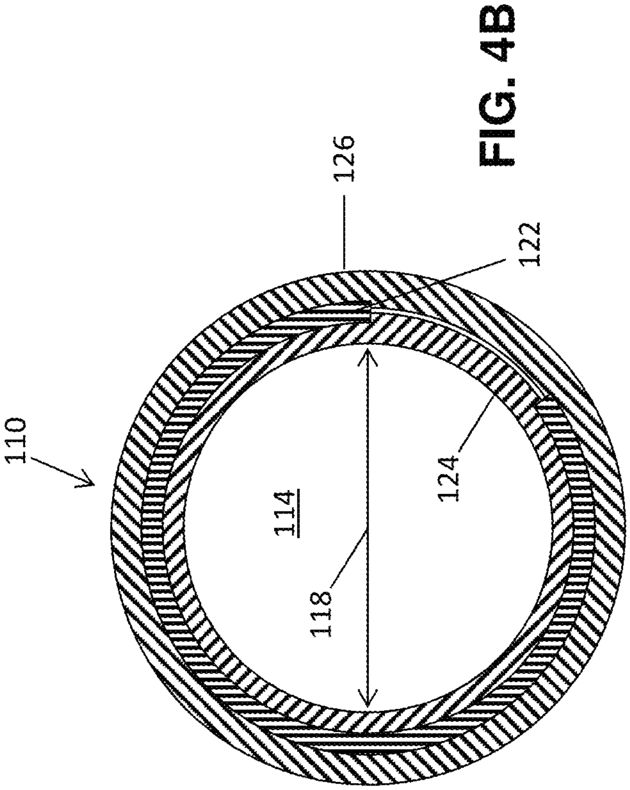
FIG. 4B is a cross section view of the catheter body taken at an arbitrary longitudinal position.

The forward end 106 of the proximal member 106 is connected to the rearward end of the catheter body 110 by a channeled strip 120 that smoothly transitions to the tapered rearward entrance 112. The catheter body 110, in the illustrated embodiment, has a coaxially layered construction. The longitudinally extending layered wall of the catheter body 110 has a resilient stiffening member 122 between at least one radially inner liner 124 and a radially outer cover 126 (FIGS. 4A-4B). The resilient stiffening member 122 is illustrated as a helical spring extending from the entrance 112 toward the distal end 102. The inner liner 124 extends within the stiffening member 122 and defines the interior surface of the interior lumen 114 of the catheter body. The outer cover 126 surrounds the stiffening member 122 and defines the exterior surface of the catheter body 110. The inner liner and outer cover respectively provide an interior surface and an exterior surface that are smoothed, and stabilize and strengthen the catheter body in cooperation with the stiffening member.

The inner liner 124 seals the stiffening member 122 from contact with fluids within the lumen 114. The inner liner 124 also facilitates sliding action of the guide device 200 along the interior of the catheter body 110 without snagging or abrasion with the stiffening member 122 when the guide device 200 and catheter 100 are assembled, for example prior to insertion into an incision and/or biological conduit, and after catheter placement when the guide device 200 is to be removed to ready the catheter for final use.

The outer cover 126 similarly seals the stiffening member 122 from contact with tissues and fluids external to the catheter 100, for example bodily fluids such as blood within a vessel. The outer cover 126 also facilitates sliding action of the catheter 100 into an incision and/or along a biological conduit or pathway.

The distal end 102 of the catheter 100 is defined by the forward terminus of the catheter body 110, where the outer cover 126 and inner liner 124 of the layered wall extend forward slightly beyond the forward terminus of the sealed stiffening member 122 (see FIG. 4A). The exterior of the distal end 102 of the catheter 100 is tapered, widening diametrically from the terminus for a short length. As represented in FIG. 4B, the interior lumen 114 of the catheter body 110 has a uniform inner diameter 118, extending from its forward opening at the distal end 102 (FIG. 4A) to the rearward entrance 112.

In the illustrated embodiment, a radiopaque marker area 130 is represented as a cylindrical area or band forward of the stiffening member 122 and near or at the distal end 102. The radiopaque area 130 facilitates visualization of the distal end 100 using medical imaging techniques during placement and use of the catheter 100. The referenced area 130 may represent a cylindrical band of material or device inserted between the outer cover 126 and inner liner 124, and rearward of the distal end 102. In a particularly novel embodiment, however, the radiopaque marker area 130 represents radiopaque doping in the material or materials that make up the catheter at or near the distal tip 102 or expressly illustrated area 130.

The stiffening member 122 extends rearward to the rearward entrance 112 of the catheter body 110 (FIG. 10). In the illustrated embodiment, stiffening member 122 and channeled strip 120 by which the catheter body 110 is connected to the proximal member 106, are contiguous portions of a same material and/or structure. A rearward portion of the strip 120 can be connected to a forward portion of the proximal member 106, for example, by welding. The handle 108 can be formed of thermoplastic overmolded onto a rearward portion of the proximal member.

The following non-limiting examples of materials are provided for thorough description only, and are not to be taken as exclusive or required materials. The stiffening member 122 can be constructed of stainless steel, such as 304 stainless steel. The inner liner and outer cover can each be constructed of polymer materials. For example, the inner liner can be constructed of, or include, polytetrafluoroethylene (PTFE), which is hydrophobic, non-wetting, and has non-stick properties to facilitate axial insertion and withdraw of the guide device when needed. The outer cover can be constructed of, or include, for example, a thermoplastic polyurethanes (TPU) such as 2362 6D Pellethane®. The radiopaque area 130 can include, as doping materials of different levels to produce different levels of radiopaque effect in imaging, one or more of platinum iridium, platinum chromium, cobalt chromium, gold, nitinol, and palladium.

Using terminology in convention with above descriptions of the catheter 100, the guide device 200 can be described as having a distal end 202 and a proximal end 204. A proximal member 206, for physical control and handling of the guide device, extends forward from the distal end 202 toward a longitudinally extending conduit member 210 along which an inner guide hole 212 (FIGS. 11, 12A) extends to receive the guidewire 50 when the guide device 200 is used to guide the catheter 100 along the guidewire. In the illustrated embodiment, the guide device 200 includes a handle 208 (FIG. 1) attached to the proximal member 206 at the proximal end 204 for comfortable and assured grip and control of the guide device 200. The proximal member 206 is illustrated as a wire that is flexible, semi-rigid, resilient, and durable.

In at least one embodiment, the handle 208 is coupled, optionally removably, to the handle 108 forming a single unit. One or more clips may be used to allow the catheter 100 and guide device 200 to be snapped together to create a single unit that can be manipulated and inserted together.

The forward end of the proximal member 206 is attached to the rearward end of the conduit member 210 and radially offset from the rearward end of the guide hole 212 (FIG. 11) to permit passage of the guidewire 50 in use. In the illustrated embodiment, an offset connector 214 attaches the proximal member 206 to the conduit member 210. The conduit member is illustrated as externally fluted, having longitudinally extending grooves 216 that permit fluid flow when the guide device 200 is present in the catheter 100 and inserted into a biological conduit such as an artery.

Figure 5:
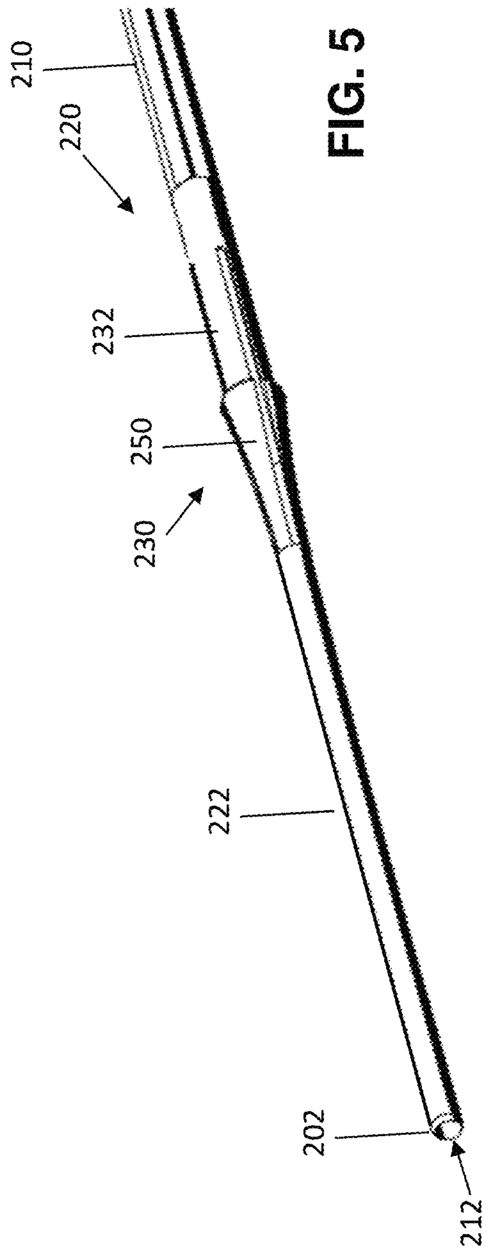
FIG. 5 is an enlarged perspective view of a distal portion of the guide device of FIG. 1.
Figure 6:
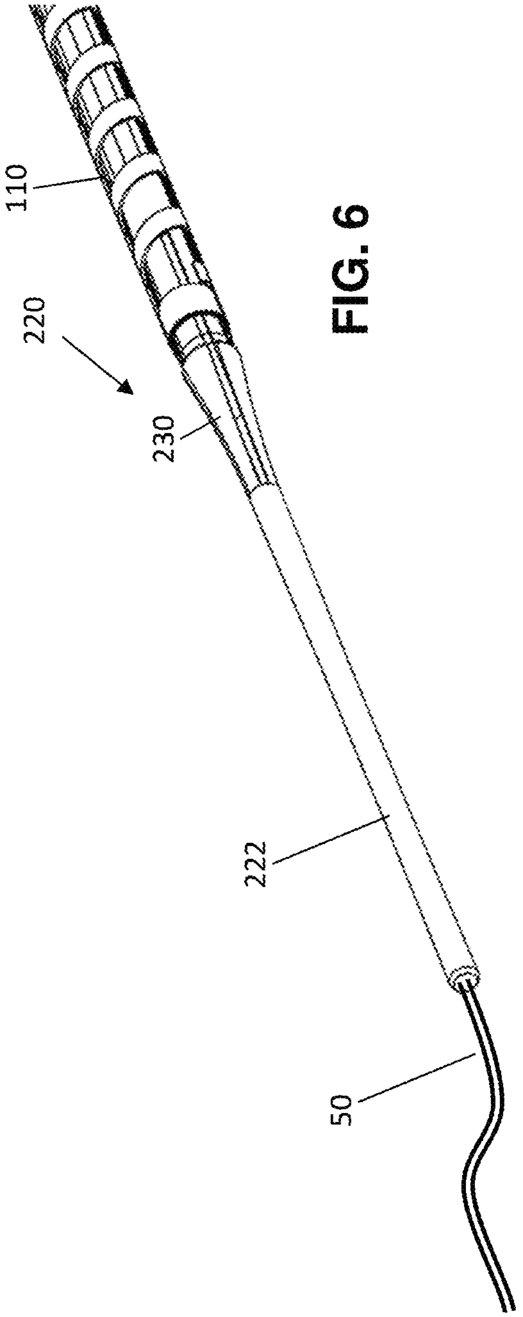
FIG. 6 is an enlarged perspective view of a distal portion of the assembly of FIG. 2.

A leading structure 220 (FIG. 5) is connected to the forward end of the conduit member 210. The leading structure 220 guides the advance of the assembled guide device 200 and catheter 100 along a guidewire 50 in use, and gently prepares tissue and biological conduits for the approaching distal end 102 of the catheter 100. The leading structure 220 includes a distal sleeve 222 and a transition section 230. The distal sleeve is illustrated as a cylindrical tube, the forward terminus of which defines the distal end 202 of the guide device. The transition section 230 is connected to and extends forward from the forward end of the conduit member 210. The distal sleeve 222 is connected to and extends forward from the forward end of the transition section 230. The guide hole 212 for receiving the guidewire 50 extends along the guide device 200 from a forward opening at the terminus of the distal sleeve 222, which defines the distal end 202 (FIG. 5), to the rearward opening at the rearward end of the conduit member 210 (FIG. 11).

Figure 11:
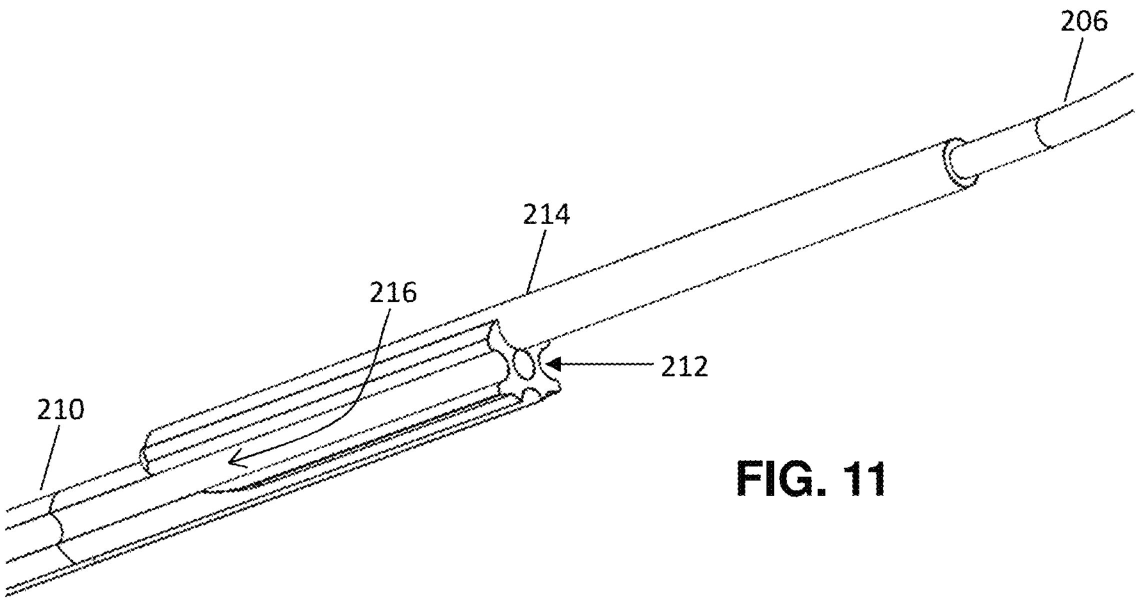
FIG. 11 is an enlarged perspective view of a portion of the guide device that positions at the junction of FIG. 9 when the guide device is inserted into the lumen of the catheter.
Figure 12A:
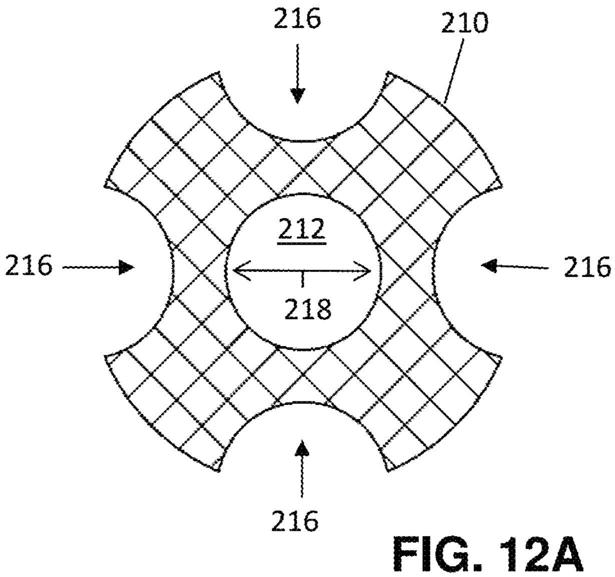
FIG. 12A is a cross section view of the conduit member of the guide device taken at an arbitrary longitudinal position.
Figure 12B:
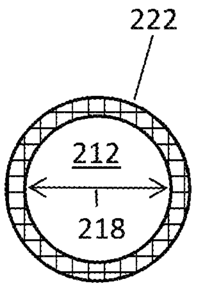
FIG. 12B is a cross section view of the forward distal sleeve of the guide device taken at an arbitrary longitudinal position.

As represented in FIGS. 12A-12B, the guide hole 212 has a uniform inner diameter 218, extending from its forward opening at the distal end 202 (FIG. 5), through the distal sleeve 222, and through the conduit member 210 to its rearward opening at the rearward end of the conduit member 210 (FIG. 11). As further shown in FIG. 12A, the grooves 216, by which the exterior of the conduit member 210 is fluted, are evenly distributed around the exterior at uniform angular spacings. In the illustrated example, in which there are four grooves 216 illustrated, the grooves 216 are evenly distributed around the exterior of the conduit member at uniform ninety-degree angular spacings.

Figure 8:
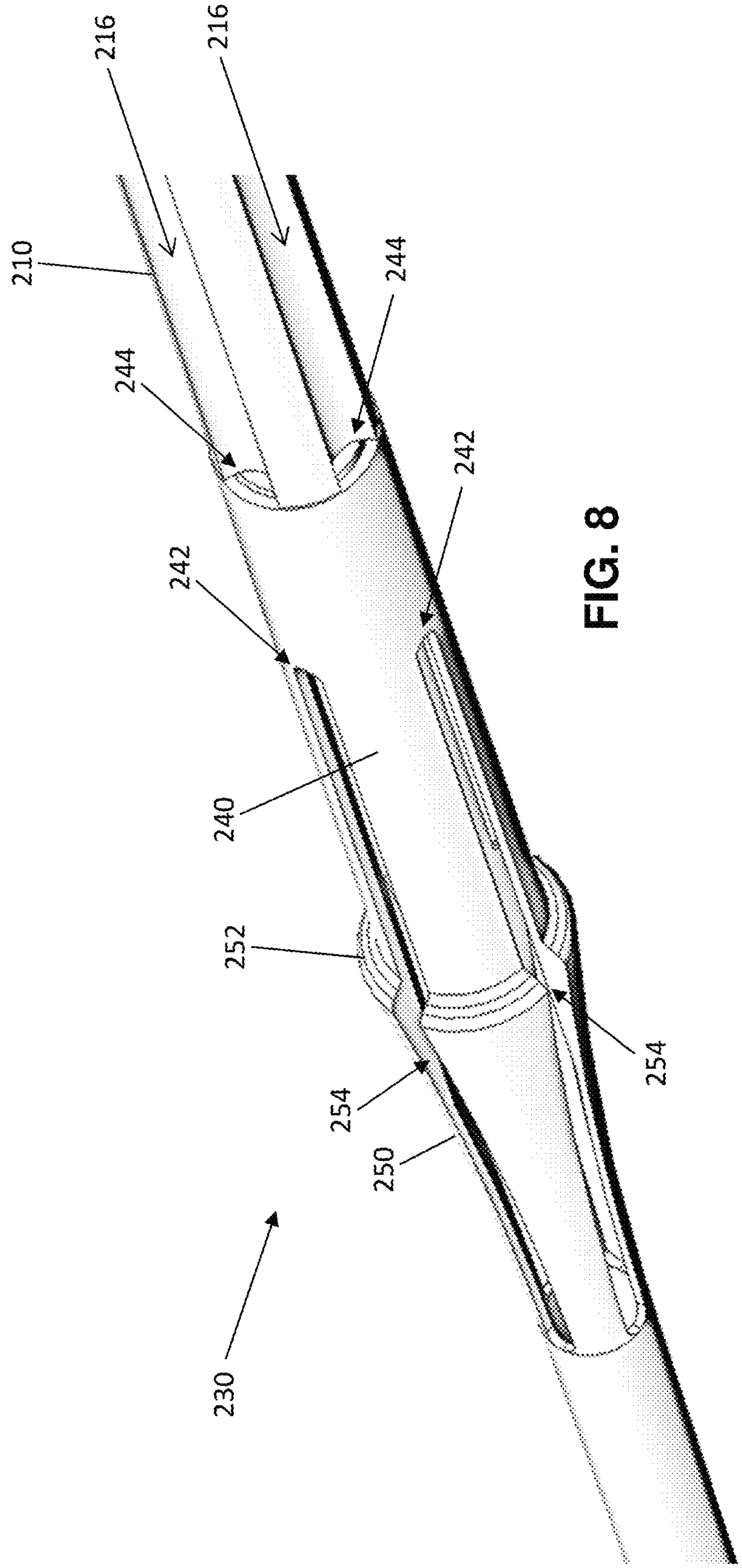
FIG. 8 is an enlarged perspective view of the rearward end of the transition section of the guide device of FIG. 1.

The transition section 230 (FIG. 8) is illustrated as having a vented barrel 240 connected to the forward end of the conduit member 210, and a forward vented frustoconical structure referenced as a cone 250, which is connected to the forward end of the barrel 240. The rearward end of the cone 250 has a shoulder 252, having an uncompressed diameter 260 which defines the greatest diameter of the cone and transition section. The cone 250 has a tapered exterior that increases diametrically from the distal sleeve 222 to the shoulder 252. The cone 250 has a progressive taper angle that increases from the sleeve to the shoulder. The tapered exterior of the cone is interrupted by longitudinally extending slots 254 that are connected for fluid passage to the grooves 216 of the fluted exterior of the conduit member.

The longitudinally extending slots 254 aligned with corresponding slots 242 defined in the exterior of a forward portion of the barrel 240. The slots 242 of the barrel 240 serve as openings into respective vents having rearward openings 244 in the rearward end of the barrel. The openings 244 are aligned with respective grooves 216 of the fluted exterior of the conduit member. This arrangement defines, from each slot 254, to a respective slot 242, to a respective opening 244, to a respective groove 216, all in one-to-one correspondence, a respective fluid channel 246 permitting fluid flow, one of which is referenced in FIG. 7A for representative illustration. Thus, even with the conduit member 210 placed in the lumen 114 of the catheter 100, fluid flow is permitted along the lumen 114 via the fluid channels 246. The openings 244 (FIG. 8) in the rearward end of the barrel slow the volume flow rate of fluid in order to safely fill a vessel with whatever the desired fluid is.

The following non-limiting examples of materials are provided for thorough description only, and are not to be taken as exclusive or required materials. The guide device 200 can consist of, or include, one or more of the following materials: polymer, polyethylene, low-density polyethylene (LDPE), and thermoplastic. The guide member, for example forward of the proximal member 206, may be formed of a single or uniform durometer material.

Like the catheter 100 having the radiopaque marker area 130, the guide device 200 can include a radiopaque marker area, for example effected by doping in the material or materials that make up the guide device, for example at or in the leading structure 220. Radiopaque doping materials of different levels can be used to produce different levels of radiopaque effect in imaging, for example to discernibly image both forward portions of the catheter 100 and forward portions of the guide device 200.

Figure 7A:
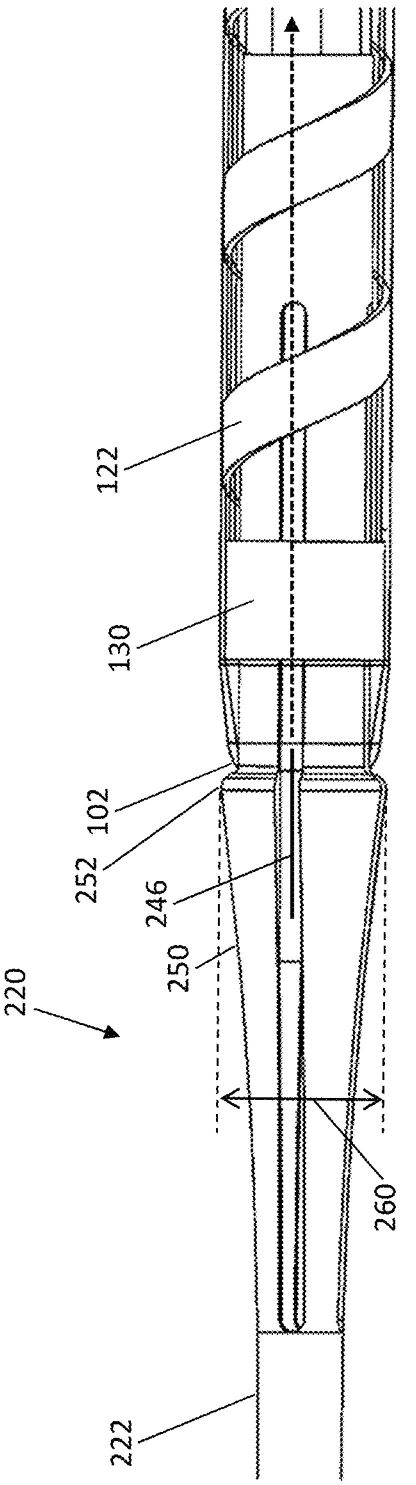
FIG. 7A is an enlarged view of the assembly of FIG. 2 at the distal end of the catheter.

To assemble the guide device 200 and catheter 100, the forward end of the guide device 200, defined by the distal sleeve 222, is inserted into the rearward entrance 112 of the catheter body 110. The channeled strip 120 can help guide the distal sleeve 222 to the tapered rearward entrance 112. The conduit member 210 is then advanced into the catheter body 110 until the distal sleeve 222 and forward cone 250 exit the distal end 102 of the catheter. Some deformation of the cone 250 and shoulder 252 thereof occurs to advance the shoulder forward through the distal end 102 of the catheter. The uncompressed outer diameter 260 (FIG. 7A) of the shoulder 252 is greater than the inner diameter 118 of the lumen 114 of the catheter body. Thus, abutment of the back of the shoulder 252 with the distal end 102 of the catheter as shown in FIG. 7A registers the insertion and assembly as complete.

Figure 9:
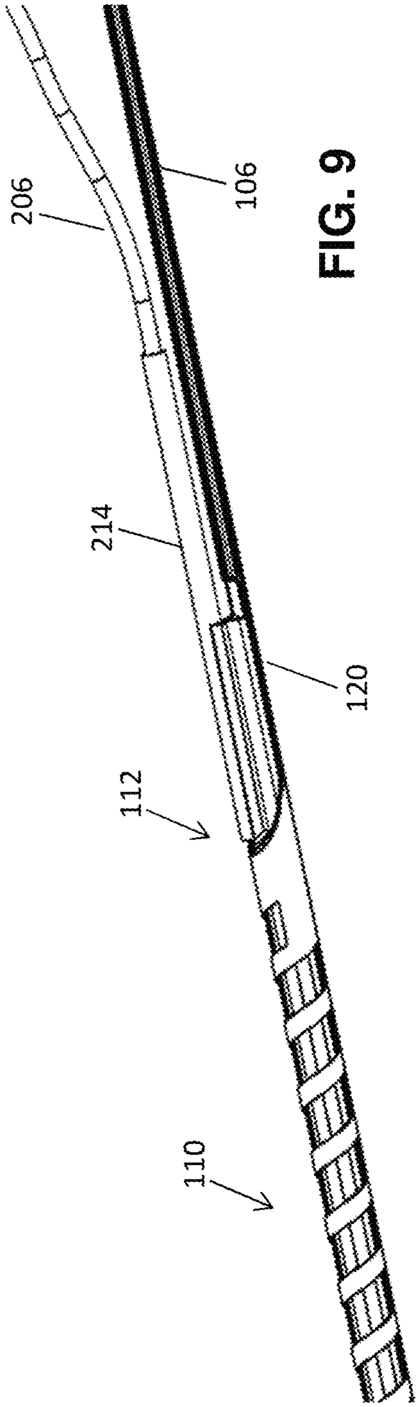
FIG. 9 is an enlarged perspective view of the junction of the guide device and catheter of FIG. 1.

When a guide device 200 and catheter 100 are well matched, the connector 214 may register at the rearward entrance 112 of the catheter body 110 as well (FIG. 9). The connector 214, where attached to the conduit member 210, serves as an insertion stop in that the connector 214 cannot enter the entrance 112 of the lumen 114 of the catheter body 110. For example, the connector 214 may have a greater diameter than the inner diameter of the lumen 114.

The system 10 can vary in length, for example from several centimeters to 1000 mm in various embodiments. The inner and outer diameters of the catheter can vary according to any use for which any particular embodiment is suited and tailored.

Figure 7B:
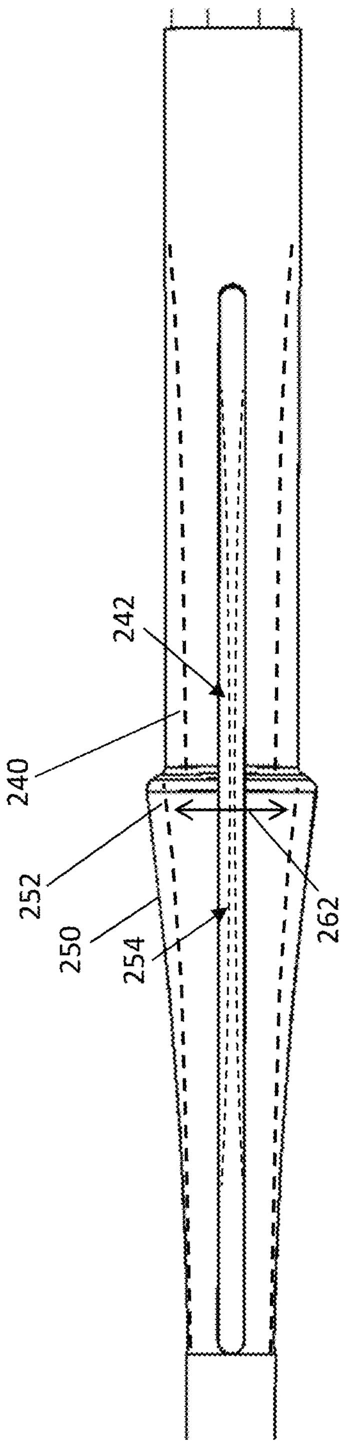
FIG. 7B is an enlarged view of a transition section of the guide device of FIG. 1, representing, in dashed line, portions thereof compressed for passage through the catheter.

As represented in FIG. 7B by dashed lines, the cone 250 is sufficiently deformable and resilient to permit deformation to pass through the distal end 102 (FIG. 7A) and into and along the interior lumen of the catheter. The outer diameter of the shoulder 252 can be reduced to a compressed diameter 262, which is less than the uncompressed diameter 260 (FIG. 7A), to squeeze through and along the interior of the catheter and through the distal end 102 thereof. The longitudinally extending slots 254 of the cone 250 and the aligned slots 242 of the barrel 240 are accordingly diminished as represented in dashed line in FIG. 7B as the cone 250 is compressed.

In use, the guide device 200 and catheter 100 can be advanced together, or with, a guidewire 50 into patient anatomy. The leading structure 220 guides the advance of the guide device 200 and catheter 100, along or with the guidewire 50, as the cone 250 serves as a diametric wedge that gently navigates soft tissues through even tortuous paths and gently expands vessels as need for passage and placement of the catheter. The guide device 200 can be removed from a placed catheter 200 by rearward withdrawal, by collapsing to fit through the opening 112 to open the lumen 114 of the catheter 100 for further use. If needed, the guide device 200 can be re-inserted to guide further advance of the catheter 100, and 230 will expand to the original diameter. These descriptions of use are not exhaustive nor limiting. These uses and advantages and others may arise as medical practitioners utilize the devices and systems expressly described and illustrated herein, and those other embodiments implied or suggested in view of the full scope of these descriptions and drawings.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. A catheter system comprising:

a catheter body that defines a longitudinally extending interior lumen; and a guide device comprising:

a conduit member for insertion into the interior lumen of the catheter body, wherein the conduit member comprises grooves;

a leading structure including a cone comprising slots, openings in the leading structure by which the slots are connected to the grooves, and a sleeve extending forward from the cone; and an inner guide hole extending longitudinally through the leading structure and the conduit member, wherein, in use, the guide device and the catheter body are coaxially arranged, the cone is forward of the catheter body, and the sleeve extends forward from the cone, and the openings slow a volume flow rate of a fluid in order to safely fill a vessel.

2. The catheter system of claim 1, wherein the cone comprises a shoulder and a tapered exterior that increases diametrically from the sleeve to the shoulder.

3. The catheter system of claim 2, wherein a back of the shoulder abuts a distal end of the catheter body to register insertion of the guide device in the catheter body.

4. The catheter system of claim 3, wherein:

an uncompressed outer diameter of the shoulder of the cone is greater than an inner diameter of the interior lumen of the catheter body; and the cone is deformable to permit deformation to pass the shoulder through the distal end and into and along the interior lumen.

5. The catheter system of claim 1, wherein the grooves extend longitudinally along an exterior of the conduit member.

6. The catheter system of claim 1, wherein the grooves are evenly distributed around an exterior of the conduit member.

7. The catheter system of claim 1, wherein the inner guide hole has a uniform inner diameter along the sleeve, the cone, and the conduit member.

8. The catheter system of claim 7, wherein:

the catheter body comprises a rearward end and an opposite distal end;

the rearward end of the catheter body has a tapered entrance; and the interior lumen extends from the tapered entrance to the distal end.

9. The catheter system of claim 8, wherein the catheter body has a longitudinally extending layered wall comprising a stiffening member, an inner liner, and an outer cover.

10. The catheter system of claim 9, wherein the stiffening member comprises a helical spring extending from the tapered entrance toward the distal end.

11. The catheter system of claim 10, wherein:

the inner liner extends within the stiffening member and defines an interior surface of the interior lumen; and the outer cover surrounds the stiffening member and defines an exterior surface of the catheter body.

12. The catheter system of claim 8, wherein the catheter body comprises a radiopaque area proximate to and at the distal end.

13. The catheter system of claim 12, wherein the radiopaque area comprises a cylindrical band between an outer cover and an inner liner and rearward of the distal end.

14. The catheter system of claim 1, wherein the guide device is removed from the catheter body by rearward withdrawal of the guide device.

* * * * *